United States Patent
Rimer et al.

(10) Patent No.: US 10,206,671 B2
(45) Date of Patent: Feb. 19, 2019

(54) ERGONOMIC ROTARY TACKER

(71) Applicants: Ofir Rimer, Kfar Truman (IL); Nir Altman, Kibbutz Kfar Etzion (IL); Shalom Levin, Atlit (IL); Asaf Levin, Atlit (IL); Izhak Fabian, Kfar Truman (IL); Aharon Cohen, Zichron Ya'akov (IL)

(72) Inventors: Ofir Rimer, Kfar Truman (IL); Nir Altman, Kibbutz Kfar Etzion (IL); Shalom Levin, Atlit (IL); Asaf Levin, Atlit (IL); Izhak Fabian, Kfar Truman (IL); Aharon Cohen, Zichron Ya'akov (IL)

(73) Assignee: THD Lap Ltd., Kfar Truman (IL)

( * ) Notice: Subject to any disclaimer, the term of this patent is extended or adjusted under 35 U.S.C. 154(b) by 185 days.

(21) Appl. No.: 15/275,667

(22) Filed: Sep. 26, 2016

(65) Prior Publication Data
US 2018/0085108 A1    Mar. 29, 2018

(51) Int. Cl.
*A61B 17/10* (2006.01)
*A61B 17/04* (2006.01)
*A61B 17/00* (2006.01)

(52) U.S. Cl.
CPC ...... *A61B 17/0401* (2013.01); *A61B 17/0469* (2013.01); *A61B 2017/00309* (2013.01); *A61B 2017/00327* (2013.01); *A61B 2017/0409* (2013.01); *A61B 2017/0464* (2013.01); *A61F 2220/0016* (2013.01)

(58) Field of Classification Search
CPC ....... A61B 17/04; A61B 17/12; A61B 17/122; A61B 17/128; A61B 17/0401; A61B 17/0469; A61B 17/10; A61F 2002/0072
See application file for complete search history.

(56) References Cited

U.S. PATENT DOCUMENTS

| | | | |
|---|---|---|---|
| 5,330,490 A | 7/1994 | Wilk | |
| 6,099,537 A * | 8/2000 | Sugai | A61B 17/0684 606/143 |
| 7,615,067 B2 * | 11/2009 | Lee | A61B 17/062 604/528 |
| 2006/0020287 A1 | 1/2006 | Lee | |
| 2007/0021737 A1 | 1/2007 | Lee | |
| 2008/0086154 A1 | 4/2008 | Taylor | |

FOREIGN PATENT DOCUMENTS

| | | |
|---|---|---|
| EP | 1908409 | 4/2008 |
| WO | 2005/079333 | 9/2005 |
| WO | 2007/136829 | 11/2007 |
| WO | 2008/008178 | 1/2008 |

* cited by examiner

*Primary Examiner* — Victor Nguyen
(74) *Attorney, Agent, or Firm* — Dekel Patent Ltd.; David Klein

(57) ABSTRACT

A tacker for applying a rotary tack, including a tacker for applying a rotary tack, including a handle with a first trigger assembly and a second trigger assembly, the trigger assemblies being coupled to an articulated applicator arm which is disposed through a drive shaft connected to the handle, the first trigger assembly operative to apply a rotary tack from a distal end of the applicator arm and the second trigger assembly operative to bend the distal end of the applicator arm, wherein a longitudinal axis of the handle is tilted with respect to the drive shaft.

9 Claims, 7 Drawing Sheets

ERGONOMIC ROTARY TACKER

CROSS-REFERENCE TO RELATED APPLICATIONS

This application is a continuation of and claims priority from U.S. patent application Ser. No. 12/427,778, filed 22 Apr. 2009, which is incorporated herein by reference.

FIELD OF THE INVENTION

The present invention relates generally to devices and methods for applying surgical fasteners, such as rotary tacks, to tissues, such as for hernia repairs and the like, and particularly to such devices and methods for use in laparoscopic and endoscopic procedures.

BACKGROUND OF THE INVENTION

A number of surgical procedures require instruments that are capable of applying a surgical fastener to tissue in order to form tissue connections or to secure objects to tissue. For example, during hernia repair it is often desirable to fasten a surgical mesh to the underlying body tissue. In laparoscopic procedures, such as for hernia repair, surgery is performed in the abdomen through a small incision, while in endoscopic procedures surgery is performed through narrow endoscopic tubes inserted through small incisions in the body. Laparoscopic and endoscopic procedures generally require long and narrow instruments capable of reaching deep within the body and configured to form a seal with the incision or tube through which they are inserted.

Some surgical techniques secure mesh to tissue or tissue to other tissue in order to effect reinforcement or repair of the tissue. A type of fastener suited for such techniques is a coil fastener having a helically coiled body portion terminating in a tissue penetrating tip, in which the helical fastener is screwed into the mesh and body tissue. An example of this type of fastener is disclosed in U.S. Pat. No. 5,258,000 to Gianturco, assigned to Cook, Inc.

U.S. patent application Ser. No. 12/022,240 to Levin and Altman, the disclosure of which is incorporated herein by reference, describes a trigger-operated mechanical tacker for applying a rotary tack. The tacker includes a drive shaft coupled to a trigger. Operating the trigger causes rotation of the drive shaft. An articulated applicator arm is pivotally connected to the drive shaft at a pivot. The articulated applicator arm includes a rotatable output shaft connected to a magazine that holds rotary tacks. The magazine is located after (distal to) the pivot. A clutch mechanism, at initial movement of the trigger, has a first orientation that causes the articulated applicator arm to pivot about the pivot until reaching a stop, and has a second orientation wherein upon continued movement of the trigger, the clutch mechanism permits the drive shaft to rotate the output shaft and cause application of the rotary tacks from the magazine.

SUMMARY OF THE INVENTION

The present invention seeks to provide devices and methods for applying surgical fasteners, such as rotary tacks, to tissues, such as for hernia repairs and the like, as is described more in detail hereinbelow. In particular, the present invention seeks to provide an improvement over the device of U.S. patent application Ser. No. 12/022,240.

There is thus provided in accordance with a non-limiting embodiment of the present invention a tacker for applying a rotary tack, including a handle with a first trigger assembly and a second trigger assembly, the trigger assemblies being coupled to an articulated applicator arm which is disposed through a drive shaft connected to the handle, the first trigger assembly operative to apply a rotary tack from a distal end of the applicator arm and the second trigger assembly operative to bend the distal end of the applicator arm, wherein a longitudinal axis of the handle is tilted with respect to the drive shaft. The first trigger assembly includes a trigger which may be tilted with respect to the drive shaft.

In accordance with a non-limiting embodiment of the present invention the distal end has partial annular cuts formed thereon so that the distal end is bendable in a first direction and generally rigid in a second direction perpendicular to the first direction, the cuts being axially spaced from each other along the distal end.

In accordance with a non-limiting embodiment of the present invention, for a given cross-section cut perpendicular to a longitudinal axis of the distal end at each partial annular cut, each partial annular cut includes first and second cuts that each extend over an angular range of less than 180° on upper and lower halves, respectively, of the cross-section of the distal end.

In accordance with a non-limiting embodiment of the present invention the first and second cuts terminate in oval terminuses perpendicular to the rest of the cut.

In accordance with a non-limiting embodiment of the present invention the trigger extends from a gear wheel which is biased by a biasing device, the gear wheel meshing through a series of gears with the applicator arm, such that squeezing the trigger towards the handle causes rotation of the distal end of the applicator arm.

In accordance with a non-limiting embodiment of the present invention the second trigger assembly is attached to the distal end of the applicator arm with at least one pull cable.

In accordance with a non-limiting embodiment of the present invention a linkage assembly is pivotally connected between the second trigger assembly and the at least one pull cable.

In accordance with a non-limiting embodiment of the present invention the linkage assembly includes a link that has a spring-loaded member that moves into a recess formed in the handle upon suitable movement of the second trigger assembly.

In accordance with a non-limiting embodiment of the present invention the tacker includes two pull cables, wherein one of the pull cables is used for bending the distal end and another of the pull cables is used for straightening the distal end.

In accordance with a non-limiting embodiment of the present invention a portion of the partial annular cuts form a spring, such that a force of the spring moves the applicator arm from a bent position to a straight position.

BRIEF DESCRIPTION OF THE DRAWINGS

The present invention will be understood and appreciated more fully from the following detailed description taken in conjunction with the drawings in which.

DETAILED DESCRIPTION OF EMBODIMENTS

Figure 1A:
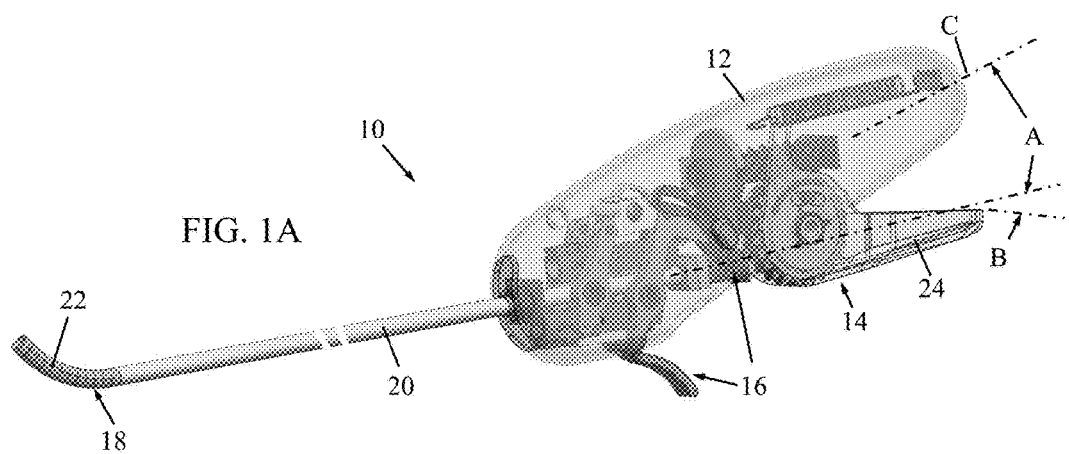
FIGS. 1A-1D are simplified pictorial illustrations of a tacker, constructed and operative in accordance with an embodiment of the present invention.

Reference is now made to FIGS. 1A-1D, which illustrate a tacker 10, constructed and operative in accordance with an embodiment of the present invention.

Tacker 10 may include a handle 12 with a first trigger assembly 14 and a second trigger assembly 16. Both trigger assemblies 14 and 16 are coupled to an articulated applicator arm 18 which is disposed through a drive shaft 20. The first trigger assembly 14 is used to apply rotary tacks (not shown in these figures) from a distal end 22 of applicator arm 18. This is accomplished by squeezing a trigger 24 towards the body of handle 12 (as shown by comparing FIGS. 1C and 1D), as will be explained more in detail hereinbelow. The second trigger assembly 16 is used to bend the distal end 22 of applicator arm 18 up (FIG. 1A) or down (FIG. 1B), as will be explained more in detail hereinbelow.

The central (longitudinal) axis C of handle 12 is tilted at an angle A in the range of about 7-25°, preferably about 11°, with respect to drive shaft 20 (that is, with respect to the proximal portion of applicator arm 18 which remains unbent), as seen in FIG. 1A. The tilted configuration of handle 12 is an important ergonomic feature of tacker 10. Prior art tackers have a pistol grip handle wherein the longitudinal axis of the handle is aligned or parallel with the drive shaft; there is no tilt. The prior art tacker is more cumbersome to use and can cause fatigue to the user. With the tilt of the present invention, tacker 10 is significantly more comfortable to use than prior art tackers. Another ergonomic feature is that trigger 24 is tilted at an angle B in the range of about 7-25°, preferably about 16°, with respect to drive shaft 20.

Figure 2A:
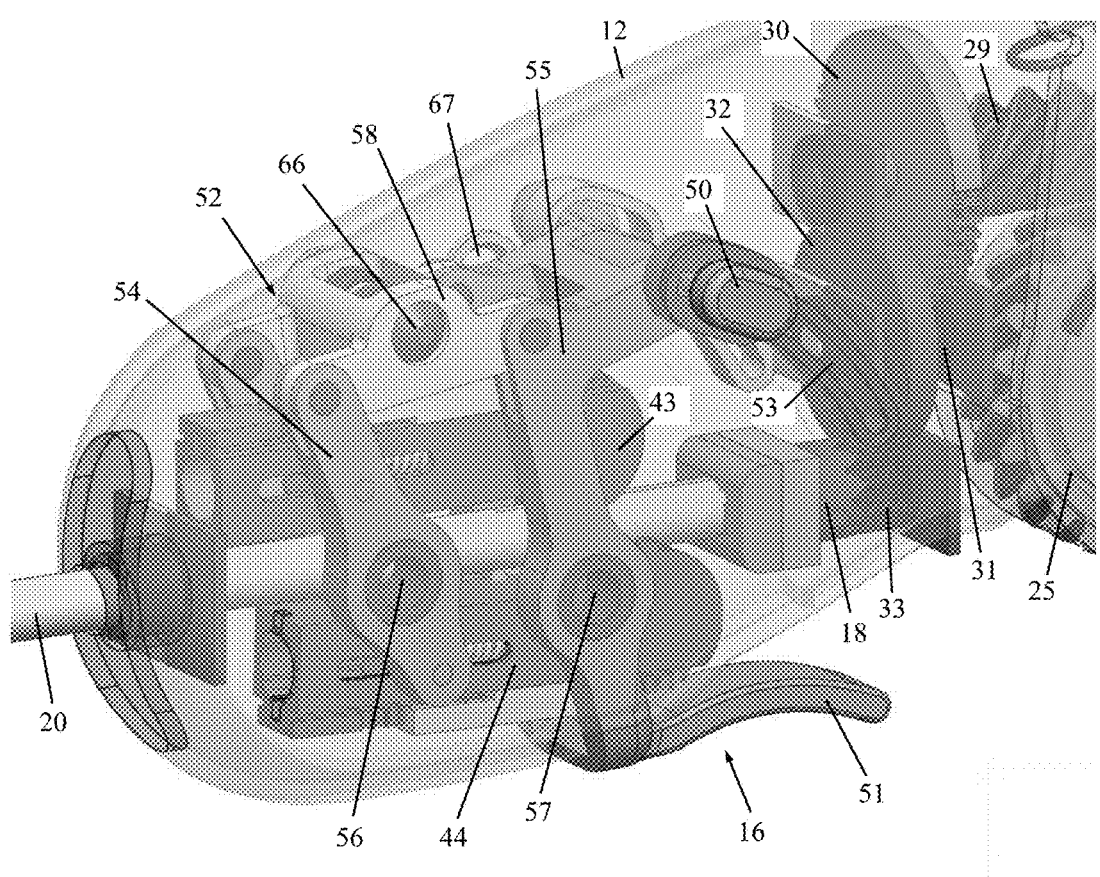
FIGS. 2A and 2B are close-up pictorial illustrations of the inner mechanism of the tacker of FIGS. 1A-1D, constructed and operative in accordance with an embodiment of the present invention.
Figure 2B:
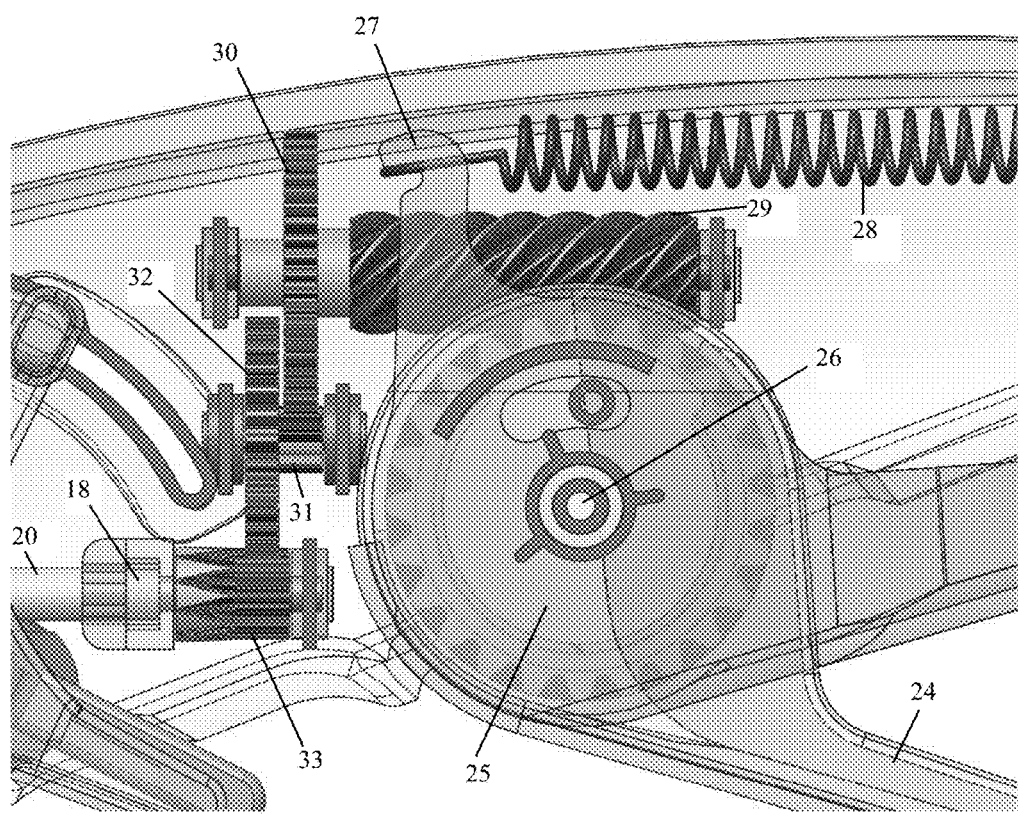
Figure 3A:
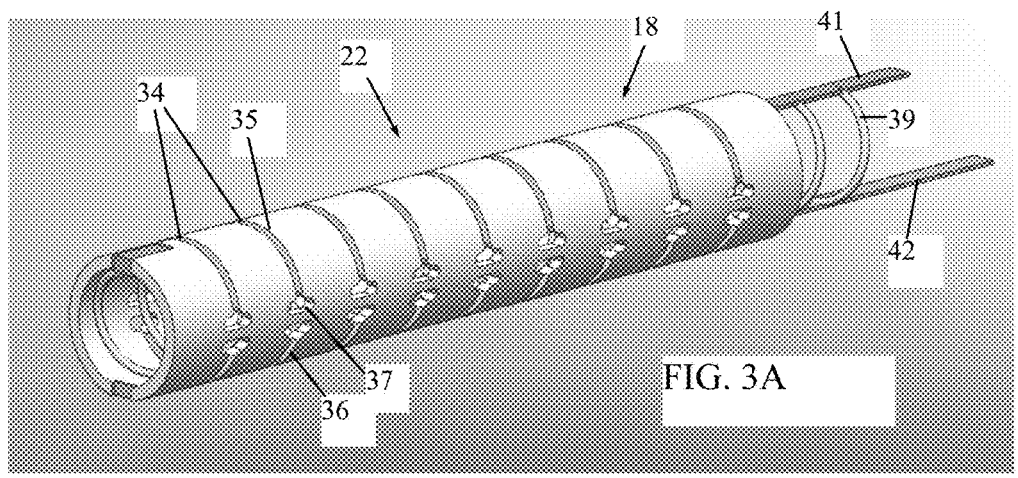
FIGS. 3A-3C and 4 are simplified pictorial illustrations of a bendable distal end of an applicator arm of the tacker, in accordance with an embodiment of the present invention.
Figure 3B:
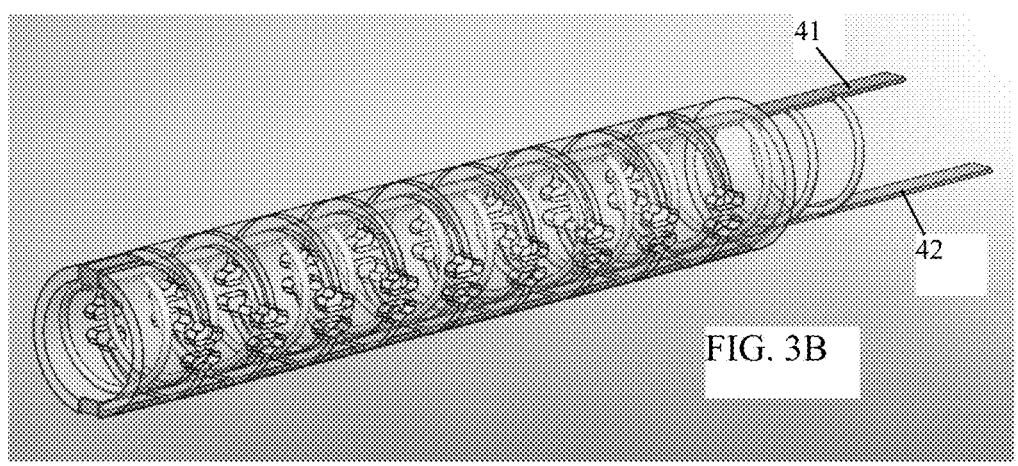
Figure 3C:
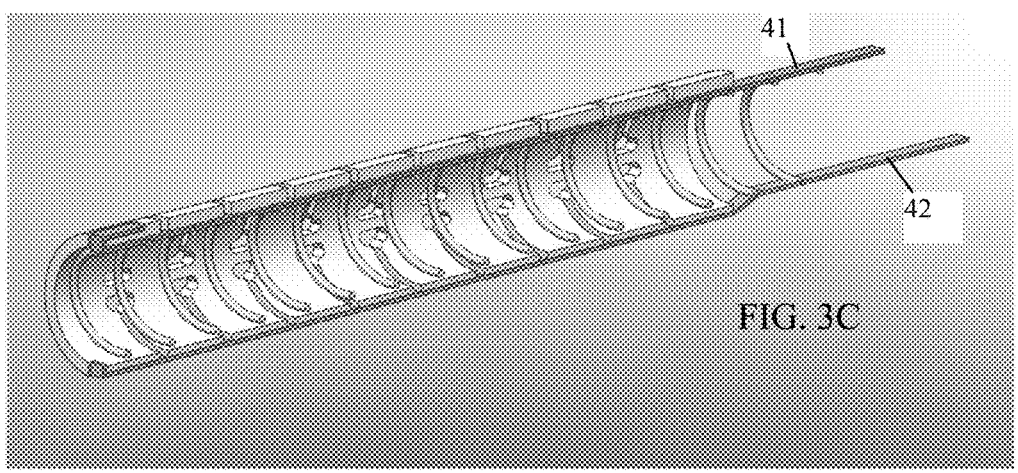

Reference is now made to FIGS. 2A and 2B, which illustrate the inner mechanism of tacker 10, in accordance with an embodiment of the present invention.

Figure 4:
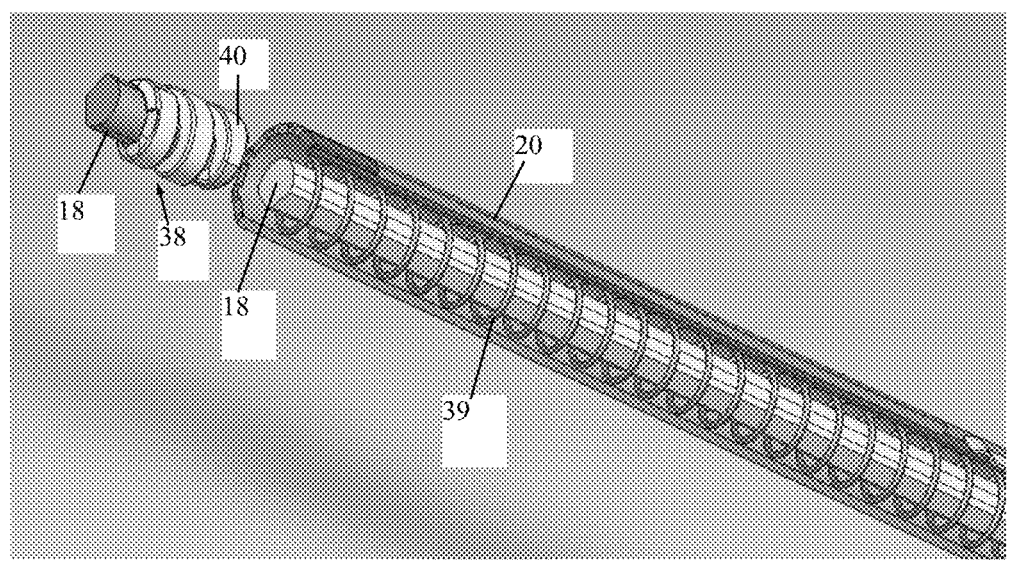

Trigger 24 extends from a gear wheel 25, which pivots about an axle 26. Gear wheel 25 has a dog 27 that extends radially outwards and is biased by a biasing device 28, such as a coil spring. Gear wheel 25 meshes with a worm gear shaft 29, which is the shaft of a gear 30. Gear 30 meshes with a short gear shaft 31 of another gear 32. Gear 32 meshes with a gear-toothed end 33 of applicator arm 18 that goes through drive shaft 20. Squeezing trigger 24 towards the body of handle 12 causes gear wheel 25 to rotate, causing worm gear shaft 29 and gear 30 to rotate, causing short gear shaft 31 and gear 32 to rotate, thereby causing gear-toothed end 33 and applicator arm 18 to rotate. Rotation of distal end 22 of applicator arm 18 causes a rotary tack 40 to advance off the distal end 22 for piercing tissue (rotary tack 40 is not shown in FIGS. 2A-2B but is seen in FIG. 4).

Squeezing trigger 24 towards the body of handle 12 extends biasing device 28. Upon releasing trigger 24, biasing device 28 pulls on dog 27, thereby causing trigger 24 to return to its nominal position for further squeezing and application of another rotary tack.

Reference is now made to FIGS. 3A-3C and 4, which illustrate the bendable distal end 22 of the applicator arm 18, in accordance with an embodiment of the present invention.

Distal end 22 is constructed of a bendable material, such as metal or plastic, with a series of partial annular cuts 34 formed thereon, such as by laser cutting, for example. The cuts 34 are formed so that distal end 22 is bendable in a first direction (e.g., up and down) and is generally rigid (not bendable) in a second direction perpendicular to the first direction (e.g., left and right). The cuts 34 are axially spaced from each other along the distal end 22. In the exemplary illustrated embodiment, for a given circular cross-section cut perpendicular to the longitudinal axis of distal end 22 at each cut 34, partial annular cuts 34 comprise first and second cuts 35 and 36 that each extend over an angular range of less than 180° on upper and lower halves, respectively, of the cross-section of the cylindrical distal end 22. The first and second cuts 35 and 36 terminate in oval terminuses 37 perpendicular to the rest of the cut. These oval terminuses 37 provide stress relief during bending of the distal end 22.

As seen in FIG. 4, one or more rotary tacks 40 are disposed on a threaded portion 38 of distal end 22 of applicator arm 18 (FIG. 4 shows the applicator arm 18 broken so as to avoid showing the entire length). The coils of tacks 40 are received in the threads of threaded portion 38. As applicator arm 18 is rotated, tacks 40 distally advance one-by-one on the threads and move off the distal end 22 of applicator arm 18 and screw into tissue (not shown). Tack 40 may have a variety of shapes, such as circular, square or rectangular, pentagonal or other shapes and combinations thereof. A biasing device 39, such as a coil spring, may be disposed at the distal end 22 to urge the tacks 40 towards the end of the arm 18.

Pull cables 41 and 42 may be attached to the upper and lower halves, respectively, of distal end 22 of applicator arm 18. Pull cables 41 and 42 are manipulated by the operator of second trigger assembly 16 to pivot articulated applicator arm 18 to any desired angle, such as up and straight (although the invention is not limited to this, and articulated applicator arm 18 can be designed for use at a variety of angles).

Figure 5A:
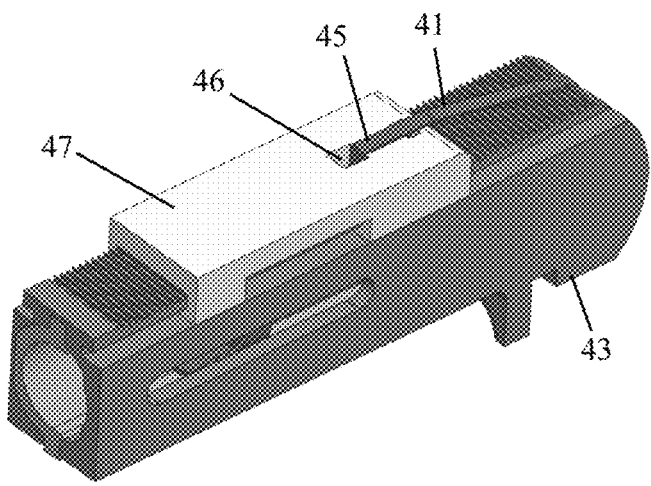
FIGS. 5A-5C are simplified pictorial illustrations of a pull cable secured to a pull block, in accordance with an embodiment of the present invention.
Figure 5B:
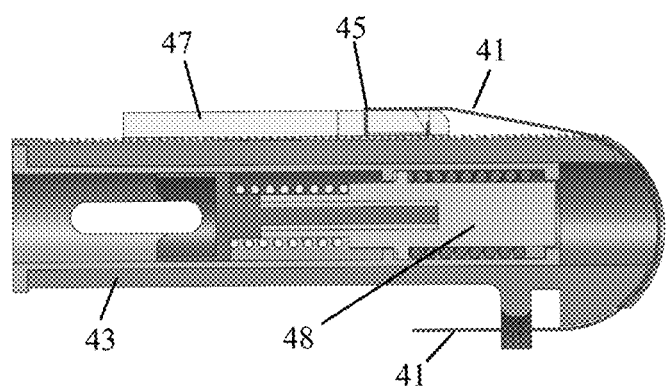
Figure 5C:
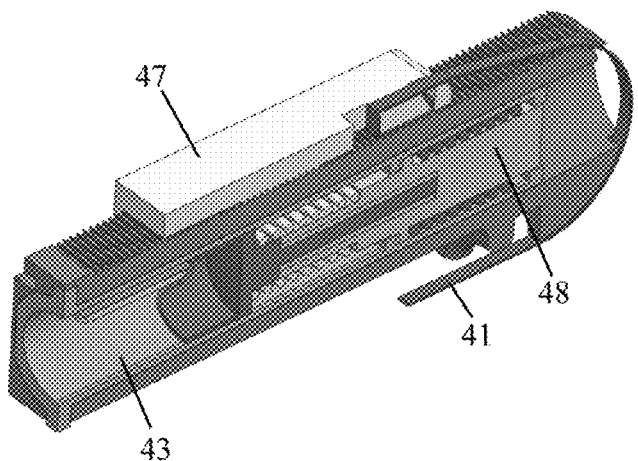

Reference is now made to 5A-5C. The proximal ends of each of the pull cables 41 and 42 are secured to pull blocks 43 and 44, respectively (FIGS. 5A-5C illustrate pull block 43, but pull block 44 is similar in construction). For example, the proximal end 45 of pull cable 41 is pulled over the rounded end of pull block 43 and secured in a slot 46 of a plate 47. Plate 47 is formed with teeth on its underside that mesh with teeth formed on the upper side of pull block 43. Plate 47 is linked to a spring-loaded piston 48 in pull block 43. In this manner, during manufacture, plate 47 can be moved over pull block 43 and locked at a desired position due to the meshing of the teeth and the spring force of spring-loaded piston 48, thus pulling pull cable 41 tightly.

Referring again to FIG. 2A, second trigger assembly 16 includes a thumb lever 50 and a finger lever 51, both of which are connected to a linkage assembly 52. Thumb lever 50 slides in an arcuate channel 53. Linkage assembly 52 is pivotally connected to pull blocks 43 and 44. In the illustrated embodiment, linkage assembly 52 includes two linkage arms 54 and 55 which pivot about pivots 56 and 57, respectively. Upper ends of linkage arms 54 and 55 are pivotally connected to each other by a link 58. Linkage arm 54 is pinned to pull blocks 43 and 44. Linkage arm 55 is connected to thumb lever 50 and finger lever 51.

Figure 1B:
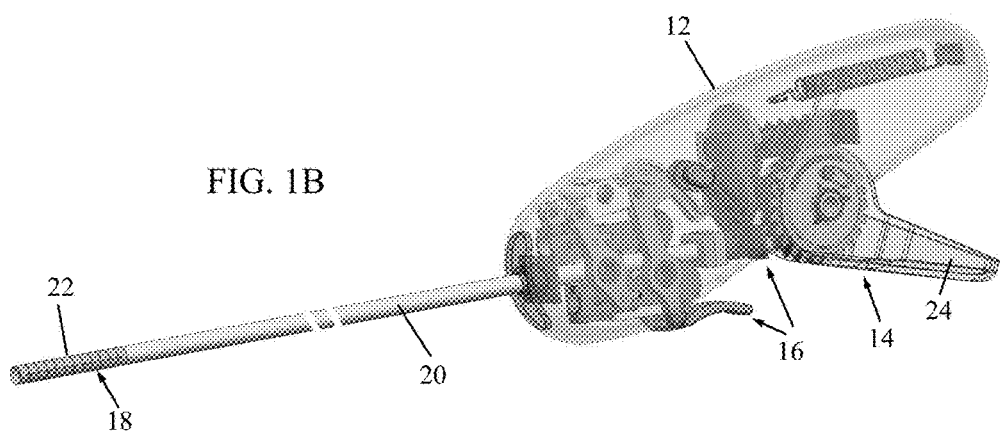
Figure 1C:
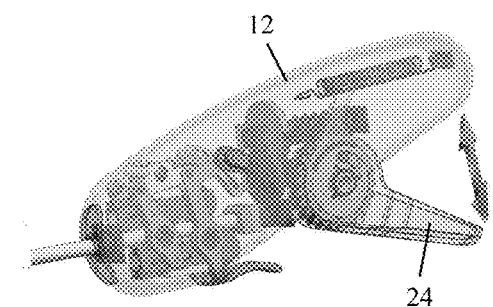
Figure 1D:
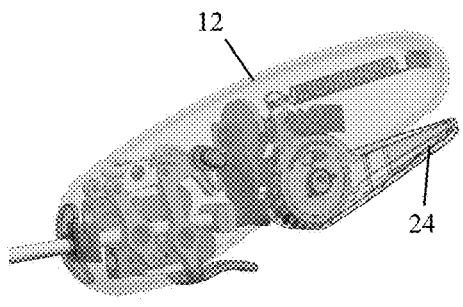

FIG. 2A (also FIG. 1B) shows thumb lever 50 and finger lever 51 in upper positions. In the upper position, the upper end of linkage arm 55 is thrust forward (distally), thereby thrusting distally the upper end of linkage arm 54. This moves pull block 44 backwards (proximally) and pulls pull cable 42 proximally to straighten the distal end 22 of applicator arm 18 (FIG. 1B). FIG. 1A shows thumb lever 50 and finger lever 51 in lower positions. In the lower position, the upper end of linkage arm 55 is pulled backward (proximally), thereby pulling proximally the upper end of linkage arm 54. This moves pull block 43 backwards (proximally) and pulls pull cable 41 proximally to bend the distal end 22 of applicator arm 18 upwards.

Link 58 is provided with a spring-loaded member 66 (e.g., rod with rounded spherical ends). When thumb lever 50 and finger lever 51 are moved to their lower positions, spring-loaded member 66 aligns with a recess 67 formed in or at the wall of handle 12, whereupon spring-loaded member 66 clicks into recess 67, due to the spring force. The end of member 66 is rounded so that when thumb lever 50 and finger lever 51 are moved away from their lower positions, member 66 easily is moved out of recess 67.

The applicator arm shown in the embodiment of FIGS. 1A-1B uses two pull cables to effect the up and down bending motion.

Reference is now made to 6A-6C, which illustrate another construction of an applicator arm 60, in accordance with another embodiment of the present invention. In this embodiment, only one pull cable is required.

Figure 6A:
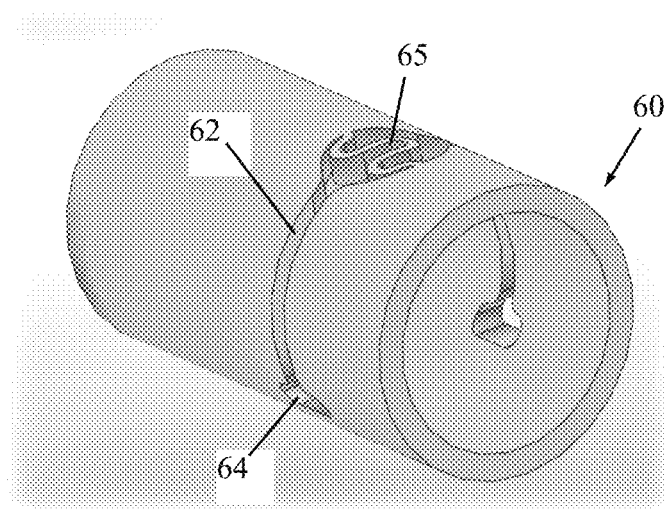
FIGS. 6A-6C are simplified pictorial illustrations of an articulated applicator arm, constructed and operative in accordance with another embodiment of the present invention.
Figure 6B:
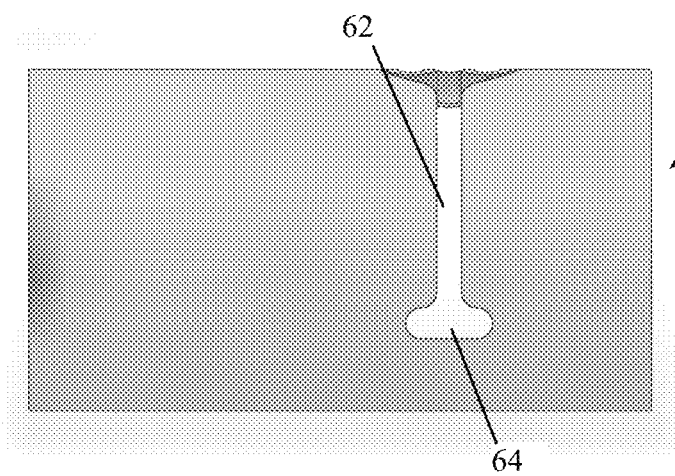
Figure 6C:
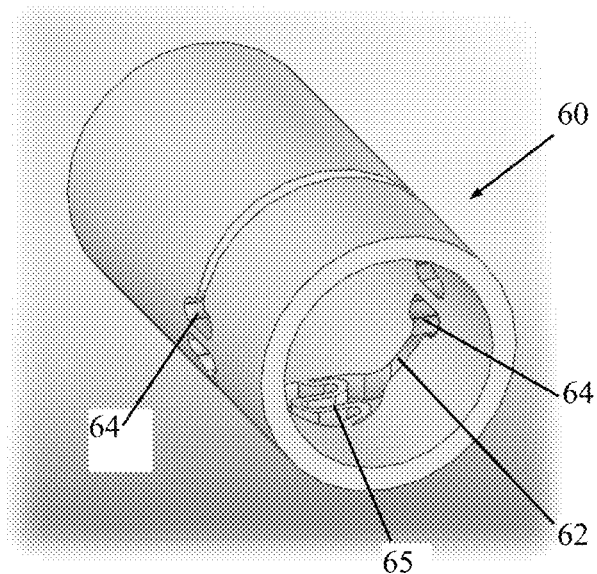

The distal end of arm 60 includes one or more partial annular cuts 62 formed thereon, such as by laser cutting, for example. FIGS. 6A and 6B show an embodiment with just one partial annular cut 62, while FIG. 6C shows an embodiment with an additional annular cut 63 at the same axial station as annular cut 62. In the embodiment of FIGS. 6A-6B, annular cut 62 extends over an angular range of more than 180°. In the embodiment of FIG. 6C, annular cuts 62 and 63 each extend over an angular range of less than 180°. The annular cuts 62 and 63 terminate in oval terminuses 64 perpendicular to the rest of the cut. These oval terminuses 64 provide stress relief during bending of the distal end of arm 60.

Annular cut 62 is formed such that a certain amount of material of the shaft of arm 60 is left to form a spring 65. Since spring 65 is part of the shaft, the spring 65 acts to straighten the shaft when thumb lever 50 and finger lever 51 are moved from their lower positions to their upper positions. Thus the applicator arm 60 is bent upwards by one pull cable (e.g., pull cable 41) but is straightened by spring 65 without need for pull cable 42.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. A tacker for applying a rotary tack, comprising:
a handle with a first trigger assembly and a second trigger assembly, said trigger assemblies being coupled to an articulated applicator arm which is disposed through a drive shaft connected to said handle, said first trigger assembly operative to apply a rotary tack from a distal end of said applicator arm and said second trigger assembly operative to bend said distal end of said applicator arm;
wherein a longitudinal axis of said handle is tilted with respect to said drive shaft;
and wherein said distal end has partial annular cuts formed thereon so that said distal end is bendable in a first direction and generally rigid in a second direction perpendicular to the first direction, said cuts being axially spaced from each other along said distal end, and wherein a portion of said partial annular cuts form a spring, such that a force of said spring moves said applicator arm from a bent position to a straight position;
wherein said second trigger assembly is attached to said distal end of said applicator arm with pull cables and one of said pull cables is used for bending said distal end and another of said pull cables is used for straightening said distal end.

2. The tacker according to claim 1, wherein the longitudinal axis of said handle is tilted about 7-25° with respect to said drive shaft.

3. The tacker according to claim 1, wherein for a given cross-section cut perpendicular to a longitudinal axis of said distal end at each partial annular cut, each partial annular cut comprises first and second cuts that each extend over an angular range of less than 180° on upper and lower halves, respectively, of the cross-section of said distal end.

4. The tacker according to claim 1, wherein said first and second cuts terminate in oval terminuses perpendicular to the rest of the cut.

5. The tacker according to claim 1, wherein a linkage assembly is pivotally connected between said second trigger assembly and said pull cables.

6. The tacker according to claim 1, wherein said second trigger assembly comprises a thumb lever and a finger lever.

7. The tacker according to claim 1, wherein said linkage assembly comprises a link that has a spring-loaded member that moves into a recess formed in said handle upon suitable movement of said second trigger assembly.

8. The tacker according to claim 1, wherein said first trigger assembly comprises a trigger tilted with respect to said drive shaft.

9. The tacker according to claim 1, wherein said trigger extends from a gear wheel which is biased by a biasing device, said gear wheel meshing through a series of gears with said applicator arm, such that squeezing said trigger towards said handle causes rotation of said distal end of said applicator arm.

* * * * *